United States Patent [19]
Canonica

[11] Patent Number: 6,047,431
[45] Date of Patent: Apr. 11, 2000

[54] METHODS AND APPARATUS FOR CLEANING CHANNELS

[75] Inventor: Francis P. Canonica, Franklin Square, N.Y.

[73] Assignee: Olympus America Inc., Melville, N.Y.

[21] Appl. No.: 08/975,690

[22] Filed: Nov. 21, 1997

[51] Int. Cl.[7] .................................................. B08B 9/06
[52] U.S. Cl. .............................. 15/104.095; 15/104.16; 15/104.2
[58] Field of Search .......................... 15/104.05, 104.09, 15/104.095, 104.16, 104.2, 104.12

[56] References Cited

U.S. PATENT DOCUMENTS

| | | |
|---|---|---|
| 2,679,061 | 5/1954 | Baker .................................. 15/104.095 |
| 4,655,627 | 4/1987 | Bradley . |
| 5,168,593 | 12/1992 | Poje ....................................... 15/104.2 |
| 5,240,675 | 8/1993 | Wilk et al. . |
| 5,251,356 | 10/1993 | Oaki et al. . |
| 5,297,310 | 3/1994 | Cox et al. . |
| 5,320,617 | 6/1994 | Leach . |
| 5,813,089 | 9/1998 | Nolan ................................. 15/104.095 |

FOREIGN PATENT DOCUMENTS

| | | |
|---|---|---|
| 4-312437 | 4/1992 | Japan . |
| 4-312441 | 4/1992 | Japan . |

Primary Examiner—Randall E. Chin
Attorney, Agent, or Firm—Straub & Pokotylo; John C. Pokotylo

[57] ABSTRACT

Methods and apparatus for cleaning a working channel using a motorized brush and cleaning fluid.

22 Claims, 8 Drawing Sheets

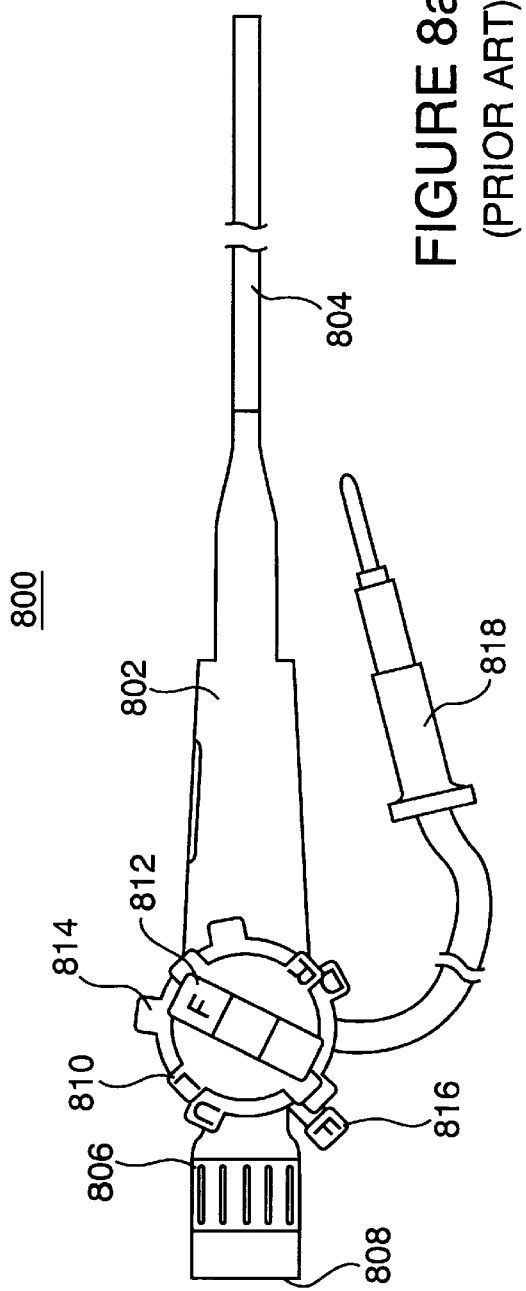
FIGURE 8a (PRIOR ART)
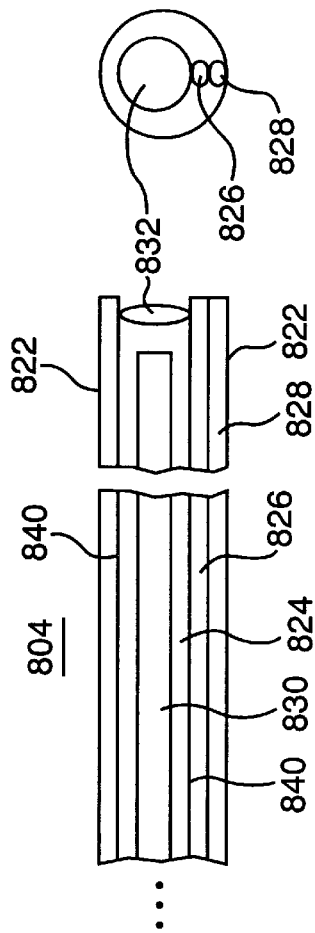
FIGURE 8c (PRIOR ART)
FIGURE 8b (PRIOR ART)

METHODS AND APPARATUS FOR CLEANING CHANNELS

BACKGROUND OF THE INVENTION

1. Field of the Invention

The present invention concerns methods and apparatus for cleaning channels or passageways, and for cleaning the working channel of an endoscope in particular.

2. Related Art

Endoscopes are medical instruments which permit minimally invasive medical examinations of, and surgery on, internal body tissues (e.g., angioscopy, arthroscopy, choledochoscopy, colonascopy, colposcopy, sinus surgery, gastroscopy, hysteroscopy, tracheal intubation, laparoscopic surgery, plastic surgery, thoracoscopy, urology, etc.). Basically, an endoscope includes an insertion tube having a distal end and a proximal end, and a scope body coupled with the proximal end of the insertion tube and having means for rendering an image captured at the distal end of the insertion tube. In medical applications, the insertion tube is inserted through a small incision or a body orifice. The insertion tube then relays an image, received at its distal end, where the image is captured within a patient's body, to its proximal end, where the image is rendered outside of the patient's body.

Although one skilled in the art understands the features and operation of flexible endoscopes, a brief description is provided below for the reader's convenience.

FIG. 8a is a side view of a flexible fiberscope 800. The flexible fiberscope 800 includes a control section 802 and an insertion tube 804. The insertion tube 804 is flexible such that its distal end may be articulated left and right, by means of left-right articulation control 810, and up and down, by means of up-down articulation control 814. The left-right articulation control 810 may be locked by brake 812, and the up-down articulation control 814 may be locked by brake 816. The control section 802 also includes a diopter adjusting ring 806 and an eyepiece 808. An adapter (not shown) may be used to connect a video camera (not shown) to the eyepiece 808. Finally, a light guide connector 818 permits connection to an external light source (not shown), as well as sources of air (or other gases) and water.

FIG. 8b is a cross-sectional side view, and FIG. 8c is an end view, of the distal end of the insertion tube 804 of the flexible fiberscope 800 of FIG. 8a. Wall 822 defines an outer cylinder and wall 840 defines an inner cylinder. Within the space 824 defined by the inner cylinder, a bundle of coherent optical fibers 830 carries an image focused on a distal end of the fiber bundle 830 by an objective lens 832. A fiberoptic or liquid light guide 826, which serve as illumination means, and working channel(s) 828, which can accommodate sensors and/or tools, are located between the inner and outer cylinders.

FIG. 9a is a side view of a flexible video endoscope 900. As with the flexible fiberscope 800 discussed above, the flexible video endoscope 900 also includes a control section 902 and a flexible insertion tube 904. The distal end of the flexible insertion tube 904 may be articulated left and right, by means of left-right articulation control 908, and up and down, by means of up-down articulation control 912. The left-right articulation control 908 may be locked by brake 910, and the up-down articulation control 912 may be locked by brake 914. Finally, a light guide and video cable 918 permits connection to an external light source (not shown), as well as sources of air (or other gases) and water via connector 920, and to a camera control unit (not shown), via connector 922.

Unlike the flexible fiberscope 800 discussed above, the video endoscope 900 does not have focus or diopter adjustment rings, nor does it have an eyepiece. This is because, as alluded to above, the video endoscope 900 provides a video output to an external camera control unit. More specifically, as shown in FIG. 9b, which is a partial cut-away, perspective view of the distal end of the insertion tube 904 of the video endoscope 900 of FIG. 9a, an objective lens 950 focuses an image 958' of an object 958 in its field of view 956, onto an imaging device, such as a charge coupled device (or "CCD") 952 for example. The CCD 952 (and associated circuitry) provides a sequence of analog waveforms based on the charge accumulated in each element of the CCD array. The camera control unit, mentioned above, converts the sequence of analog waveforms to frames of video, which may comply with the NTSC, PAL or S video standard for example.

The flexible video endoscope 900 may also include an illumination channel 930 terminating at window 932 and a working channel(s) 940 terminating at distal opening(s) 942.

Though not discussed in detail here, some endoscopes may have rigid, straight, insertion tubes in which an image focused at the distal end is conveyed, via a lens system, to the proximal end. Such endoscopes may also employ illumination channels and working channels.

As alluded to above, many endoscopes include working channels. Depending upon the application of the particular endoscope, various tools may be passed through the working channel. These tools will extend out from the distal end of the insertion tube and may be manipulated by a user at the proximal end on the endoscope. For example, knives, curettes, forceps, scissors, and cauterizing electrodes may be passed through the working channel. Moreover, pressurized gas may be passed via a working channel to insufflate a body cavity, fluid may be passed via a working channel to irrigate a body cavity, and a negative pressure may be introduced to the working channel to suck out irrigation fluid, tissue, or body fluids.

Endoscopes are relatively expensive and thus are typically reused many times. Naturally, between uses, the endoscopes must be cleaned and disinfected or sterilized. For example, when reprocessing the endoscope for use on a next patient, the working channels must be cleaned and disinfected or sterilized. Since, in general, the working channels cannot be visually inspected, there is no direct way of ensuring that they have been adequately cleaned and sterilized. Thus, rigid and time consuming protocols for cleaning the working channels are often implemented. Such a cleaning protocol is discussed below with reference to FIG. 10.

FIG. 10 is a side view of a channel brush 1000 for cleaning the working channel of an endoscope. The channel brush 1000 includes a ring 1010 to be grasped or manipulated with a user's finger(s). A proximal end of a flexible shaft 1020 is attached to the ring 1010. The length of the flexible shaft must be at least as long as the working channel in the insertion tube of the endoscope. A distal end of the flexible shaft 1020 may be provided with a relatively rigid section 1022, a relatively flexible section 1024, and another relatively rigid section 1026. A brush section 1030, typically nylon fibers held in twisted metal wires, is attached to (e.g., by means of soldering, welding, etc.) the second relatively rigid section 1026. A rounded end 1040 is provided to protect the walls of the working channel from the wire ends of the brush section 1030. Another brush for cleaning endoscopes is discussed in U.S. Pat. No. 5,297,310 (incorporated herein by reference). In a typical cleaning protocol, the brush is passed through the detergent-filled working channel of the endoscope three (3) times, during which it is articulated back and forth with shorter strokes. Then the working channel is rinsed and subsequently either flushed with disinfectants or sterilized in an attempt to reprocess the working channel.

The above described reprocessing protocol has a number of disadvantages. First, the manual operation is time consuming. Consequently, the endoscope, a relatively expensive medical resource, is unavailable for use on another patient during reprocessing (also referred to as "endoscope downtime"). Similarly, the person performing the reprocessing is also unavailable to perform other tasks. Second, human training and care may greatly affect the efficacy of the reprocessing protocol.

A number of inventions have been presented in an effort to improve the reprocessing of medical endoscopes. For example, Japanese Patent No. 4-312437, and corresponding U.S. Pat. No. 5,251,356 (incorporated herein by reference) (hereafter referred to as "the Oaki patents"), disclose a motorized brush for cleaning the working channel of an endoscope in which the brush may be rotated and reciprocated. While it is believed that the Oaki patents provide an excellent tool for cleaning the working channels of endoscopes, sterilizing or disinfecting the endoscope is not directly addressed. Japanese Patent No. 4-312441 discloses a motorized brush and insertion tube guide assembly for cleaning the working channels of endoscopes. This patent also discloses a brush used in conjunction with a loop insertion tube guide and a reservoir for cleaning working channels of endoscopes.

U.S. Pat. No. 5,240,675 (hereafter referred to as "the Wilk patent" and incorporated herein by reference) discusses a tool for cleaning and sterilizing the working channels of endoscopes. The tool discussed in the Wilk patent uses radiation and/or heat to sterilize the working channel. A brush and sterilizing fluid may also be used to clean and sterilize the working channel. The brush may be vibrated by means of ultrasonic waves. Unfortunately, it is believed that the vibrating motion of the brush induced by the ultrasonic waves does not clean as thoroughly as a rotating brush.

In view of the above limitations of the known tools for reprocessing endoscopes, and cleaning and sterilizing working channels in particular, an improved tool is needed. Such a tool should thoroughly clean the working channel(s) of an endoscope. It should provide good abrasion of debris from channel surfaces. Finally, it should be simple and relatively quick to use, and it should be relatively portable.

SUMMARY OF THE INVENTION

The present invention provides a device for cleaning a channel. The device comprising a motor, a gas pressurizing unit, a fluid reservoir, a flexible drive shaft, a brush head assembly, a flexible sheath and a dynamic seal. The motor has a power take off. The fluid reservoir has an inlet and an outlet. The inlet is fluidly coupled with the gas pressurizing unit. The flexible drive shaft has a first end, connected with the power take off of the motor, and a second end coupled with the brush head assembly. The flexible drive shaft extends through the flexible sheath. The flexible sheath has a fluid inlet port fluidly coupled with the outlet of the fluid reservoir. The flexible drive shaft extends through the dynamic seal. The dynamic seal serves to seal an end of the flexible tubular sheath.

The device may also include means for controlling the motor and/or means for controlling the gas pressurizing unit. The means for controlling may be a foot actuated controller for controlling the motor and/or the gas pressurizing unit.

The first end of the flexible drive shaft may be connected with the power take off of the motor by means of a chuck.

The flexible sheath may be a Teflon tube. The fluid inlet port of the flexible sheath may be a luer lock connector. The flexible sheath may include markings for indicating an insertion depth.

The fluid reservoir may include a first fluid reservoir for containing flushing fluid, and a second fluid reservoir for containing cleaning fluid. Means for selecting a fluid source including (i) a first inlet fluidly coupled with an outlet of the first fluid reservoir, (ii) a second inlet fluidly coupled with an outlet of the second fluid reservoir, (iii) an outlet fluidly coupled with the fluid inlet port of the flexible sheath, and (iv) a selector for fluidly coupling the first and/or second fluid inlet to the outlet, may also be provided.

The brush head assembly may include (i) a proximal end connected with the second end of the flexible drive shaft, (ii) a distal end, (iii) a first brush of coarse, stiff, bristles, and (iv) a second brush of fine, soft, bristles, wherein the first brush is arranged on the brush head assembly between the distal end and the second brush. The brush head assembly may be connected with the second end of the flexible drive shaft by means of a friction fit. Alternatively, or in addition, the brush head assembly and the second end of the flexible drive shaft may have mating cross sectional shapes such that rotational slip between the flexible drive shaft and the brush head assembly is prevented. Alternatively, the brush head assembly may be connected with the second end of the flexible drive shaft by means of a threaded connection. In yet another alternative embodiment, the brush head assembly may be connected with the second end of the flexible drive shaft by means of a crimped connection.

The present invention also provides a device for use with a system for cleaning a channel. The device includes a flexible drive shaft, a flexible sheath, and a dynamic seal. The flexible drive shaft has a first end and a second end and extends through the flexible sheath. The flexible sheath has (i) a first end through which the first end of the flexible drive shaft extends, (ii) a second end through which the second end of the flexible drive shaft extends, and (iii) a fluid inlet port arranged closer to the first end of the flexible sheath than the second end of the flexible sheath. The dynamic seal is provided on the first end of the flexible sheath. The first end of the flexible drive shaft extends through the dynamic seal.

The present invention also provides a method for cleaning a working channel of an endoscope with a device including a flexible drive shaft, a controllable motor having a power take off, a controllable gas pressurizing unit, a cleaning fluid reservoir having an inlet and an outlet, a brush head assembly, and a flexible sheath, through which the flexible drive shaft extends, having a fluid inlet port. The method includes steps of (a) connecting the inlet of the cleaning fluid reservoir to the controllable gas pressurizing unit, (b) connecting the brush head assembly to a distal end of the flexible drive shaft, (c) connecting a proximal end of the flexible drive shaft with the power take off of the motor, (d) coupling the fluid inlet port of the flexible sheath with the outlet of the cleaning fluid reservoir, (e) starting the motor, (f) inserting the brush head into an end of the working channel, (g) activating the gas pressurizing unit, and (h) passing the brush head assembly through the working channel.

Finally, the present invention provides a method for cleaning a working channel of an endoscope with a device including a flexible drive shaft, a controllable motor having a power take off, a controllable gas pressurizing unit, a cleaning fluid reservoir having an inlet and an outlet, a flushing fluid reservoir having an inlet and an outlet, a source selection means having a first inlet coupled with the outlet of the cleaning fluid reservoir, a second inlet coupled with the outlet of the flushing fluid reservoir, an outlet, and a selector, a brush head assembly, and a flexible sheath, through which the flexible drive shaft extends, having a fluid inlet port. The method includes steps of (a) connecting the inlets of the cleaning fluid and flushing fluid reservoirs to the controllable gas pressurizing unit, (b) connecting the brush head assembly to a distal end of the flexible drive shaft, (c) connecting a proximal end of the flexible drive shaft with the power take off of the motor, (d) coupling the fluid inlet port of the flexible sheath with the outlet of the means for selecting, (e) starting the motor, (f) inserting the brush head into an end of the working channel, (g) activating the gas pressurizing unit, (h) setting the selector of the means for selecting such that the outlet of the means for selecting is fluidly coupled with the first inlet of the means for selecting, (i) passing the brush head assembly through the working channel, (j) setting the selector of the means for selecting such that the outlet of the means for selecting is fluidly coupled with the second inlet of the means for selecting, and (k) pulling the brush head assembly back through, and out of, the working channel.

BRIEF DESCRIPTION OF THE DRAWINGS

FIG. 8a depicts a conventional flexible fiberscope with which the present invention may be used. FIG. 8b is a cross-sectional side view of a portion of an insertion tube of the flexible fiberscope of FIG. 8a.

FIG. 8c is an end view of the distal end of the insertion tube of FIG. 8b.

FIG. 9b is a partial cross-sectional perspective view of a distal end of an insertion tube of the flexible video scope of FIG. 9a.

DETAILED DESCRIPTION

The present invention concerns a novel tool for cleaning the working channels of endoscopes during the reprocessing of the endoscopes. The following description is presented to enable one skilled in the art to make and use the invention, and is provided in the context of a particular application and its requirements. Various modifications to the disclosed embodiments will be apparent to those skilled in the art, and the general principles set forth below may be applied to other embodiments and applications. Thus, the present invention is not intended to be limited to the embodiment shown.

In the following, functions of the present invention will be described first. Then, the structure of an exemplary system which embodies the present invention will be described. Details of exemplary system components will then be described. Finally, the operation of the system will be described.

FUNCTIONS OF THE INVENTION

The present invention thoroughly cleans the working channels of endoscopes, while simplifying the endoscope reprocessing protocol and reducing the time required for endoscope reprocessing. The present invention provides a tool which rotates a cleaning brush and dispenses detergent for cleaning the working channel. By both rotating the cleaning brush and dispensing detergent, abrasion of the internal channel walls and contact with commonly employed, low-foaming, medical grade detergents are enhanced.

STRUCTURE OF THE INVENTION

Having described functions of the present invention, an exemplary system which embodies the present invention, as well as detailed descriptions of exemplary system components, will now be described.

Figure 1:
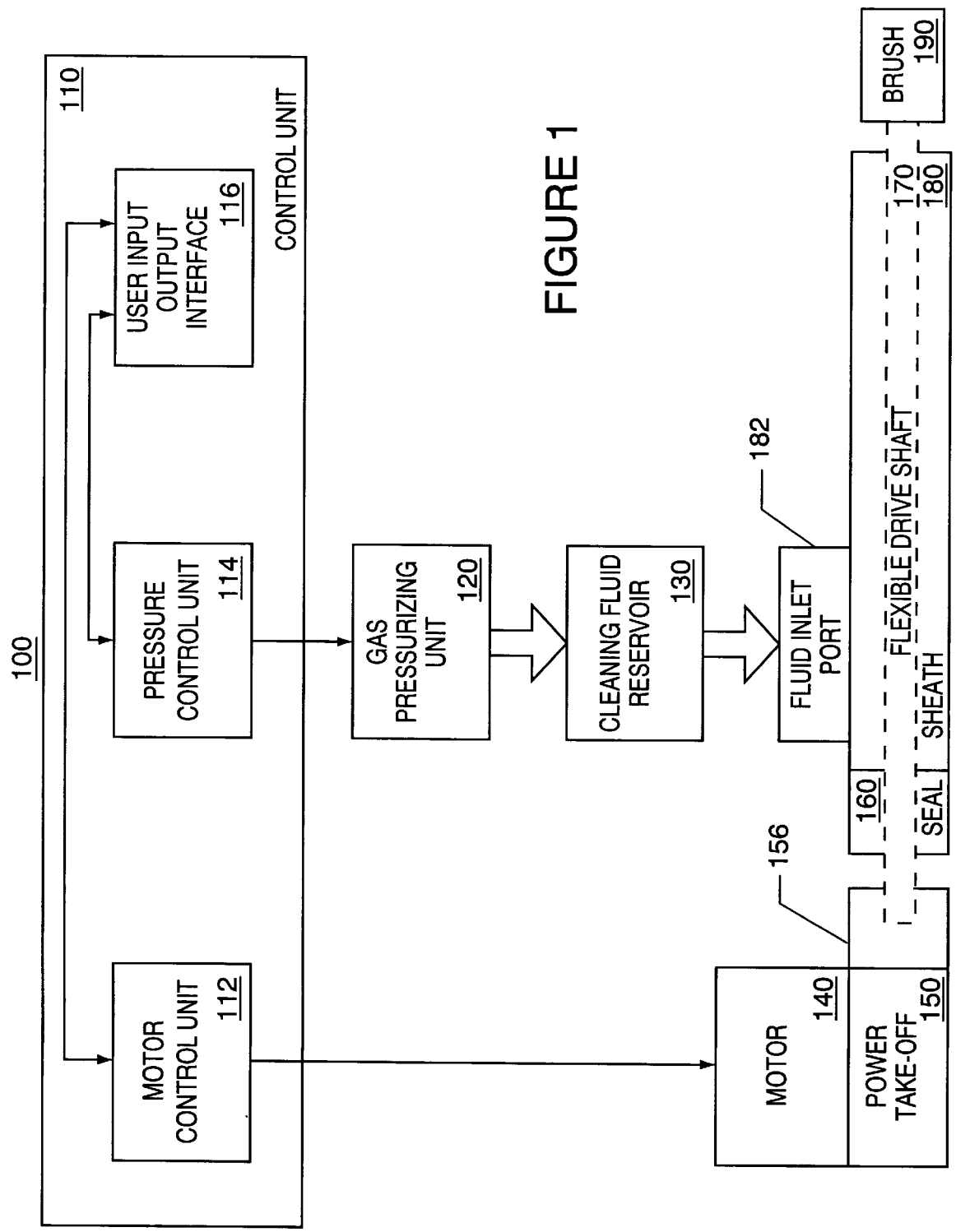
FIG. 1 is a high level block diagram of a system which embodies the present invention.

FIG. 1 is a high level block diagram of an exemplary system 100 which embodies the present invention. The system 100 includes a control unit 110, a motor 140 having a power take off 150, a gas pressurizing unit 120, a reservoir of cleaning fluid 130, and an assembly having a power take off coupling 156, a fluid inlet port 182, a dynamic seal 160, a flexible drive shaft 170, a sheath 180, and a brush 190. The flexible drive shaft 170 has a first (proximal) end releasably coupled with the power take off coupling 156, and a second (distal) end to which the brush 190 is attached. Most of the flexible drive shaft 170 is contained within the sheath 180 and a proximal section of the flexible drive shaft extends through the seal 160. The control unit 110 includes a user input/output interface 116 for controlling a motor control unit 112 and a pressure control unit 114. The motor control unit 112 provides control signals to the motor 140, such as speed (e.g., RPM) control and/or ON-OFF signals for example. The pressure control unit 114 provides control signals to the gas pressurizing unit 120, such as ON-OFF signals for example. The gas pressuring unit 120 provides pressurized gas to the cleaning fluid reservoir 130 which, in turn, provides cleaning fluid to the fluid inlet port 182 of the assembly. The fluid is contained by the dynamic seal 160 and the sheath 180 such that it exits the sheath 180 at its the distal end, in close proximity to the brush 190.

Having described an exemplary system 100 which embodies the present invention, exemplary system components are now described.

Figure 2:
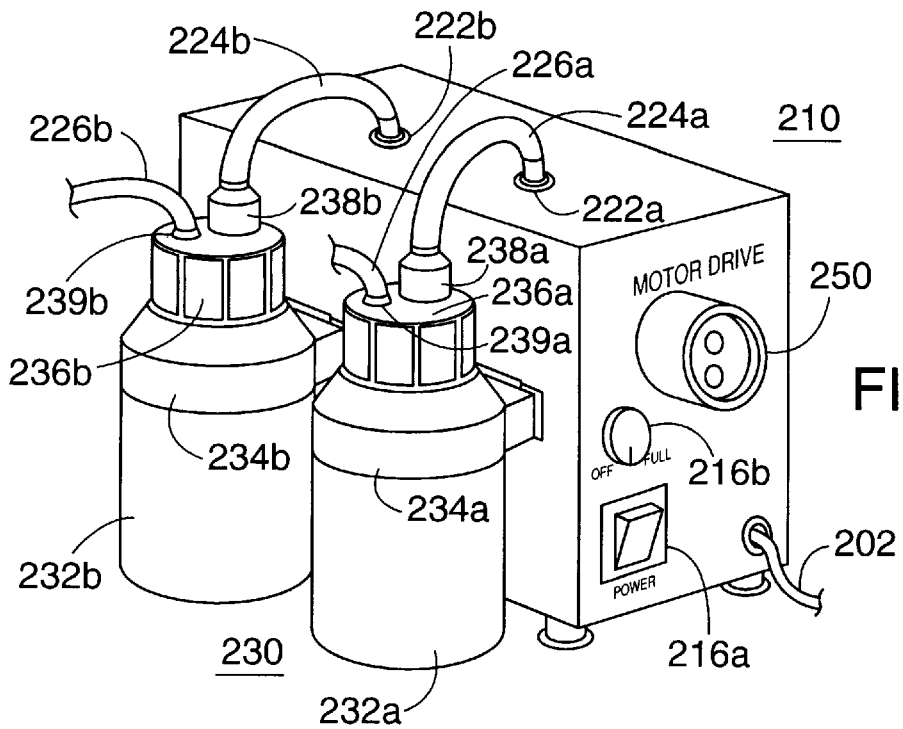
FIG. 2 depicts exemplary components of the system of FIG. 1.

FIG. 2 is a perspective view of an exemplary control unit, motor, power take off, gas pressurizing unit, and cleaning fluid and flushing fluid reservoirs which may be used in the system 100 of FIG. 1. Referring to FIG. 2, a housing 210 accommodates a motor control unit, a motor, a pressure control unit, and a gas pressuring unit, none of which are shown. These units are may be powered by an AC outlet via power cord 202. The housing 210 may be based on a modified endoscope maintenance unit used for detecting leaks in endoscopes and for flushing endoscopes, such as Product Number MU-1, sold by Olympus Optical Co. Ltd. of Tokyo, Japan.

As shown in FIG. 2, the user input/output interface may be as simple as an ON-OFF power switch 216a, and a motor speed control knob 216b having labels and an appropriate position indicator. The speed of the motor may be varied between 0 and 100 RPM. Naturally, the user input/output interface may be more complex, and may be embodied by a touch sensitive video display having a graphical user interface or a microprocessor based control interface for example.

Figure 4:
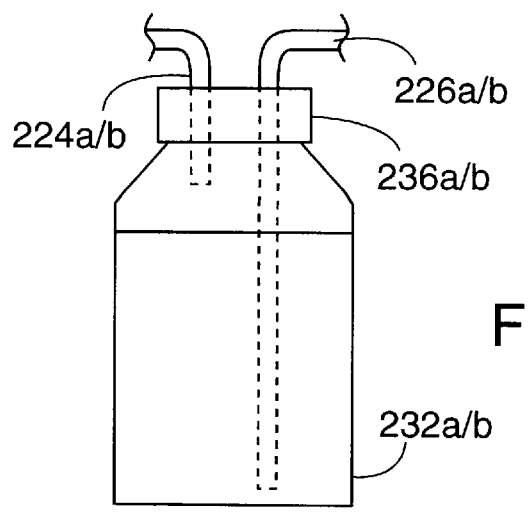
FIG. 4 is a cross-sectional side view of a cleaning/sterilizing fluid or flushing fluid reservoir shown in FIG. 2.

The cleaning fluid and/or flushing fluid reservoir 230 may include a first bottle 232a, held to the housing 210 by means of a flexible (e.g., plastic, or fabric) strap 234a, and a similar second bottle 232b, held to the housing 210 by means of a second flexible strap 234b. One bottle may hold flushing fluid, such as water, while another bottle may hold cleaning fluid, such as a detergent. Each bottle 232a/232b includes a cap 236a/236b which may close the bottle in a substantially air-tight manner. Each cap 236a/236b includes a gas inlet port 238a/238b, which is fluidly coupled, by means of tubing 224a/224b, to pressurized gas outlet ports 222a/222b on the housing 210. The gas pressuring unit 120 (not shown) internal to the housing 210 provides the pressurized gas. Each cap 236a/236b also includes a fluid outlet opening 239a/239b through which tubing 226a/226b extends. As shown in the cross-section view of FIG. 4, the tubing 226a/226b extends down into the fluid held in the bottle 232a/232b such that when pressurized gas is introduced into the bottle 232a/232b via port 224a/224b, fluid held in the bottle 232a/232b is forced out of the bottle 232a/232b through the tubing 226a/226b.

Figure 3:
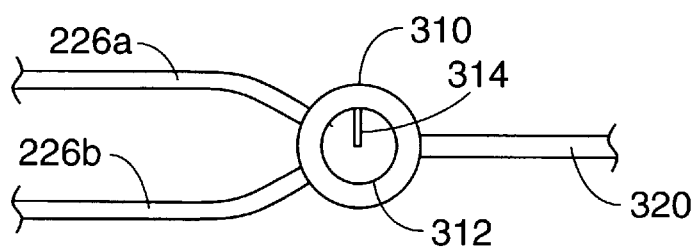
FIG. 3 depicts exemplary components of the system of FIG. 1.

If two fluid reservoirs are used, such as a flushing fluid reservoir and a cleaning fluid reservoir as is shown in FIG. 2, then, as shown in FIG. 3, a source selection means 310 may be used to select (a) fluid in line 226a from bottle 232a, (b) fluid in line 226b from bottle 232b, (c) fluid in both lines 226a and 226b from bottles 232a and 232b, respectively, or (d) no fluid, to be provided to line 320. The selection means 310 may include a selection dial 312 having a visual selection indicator 314.

Figure 5:
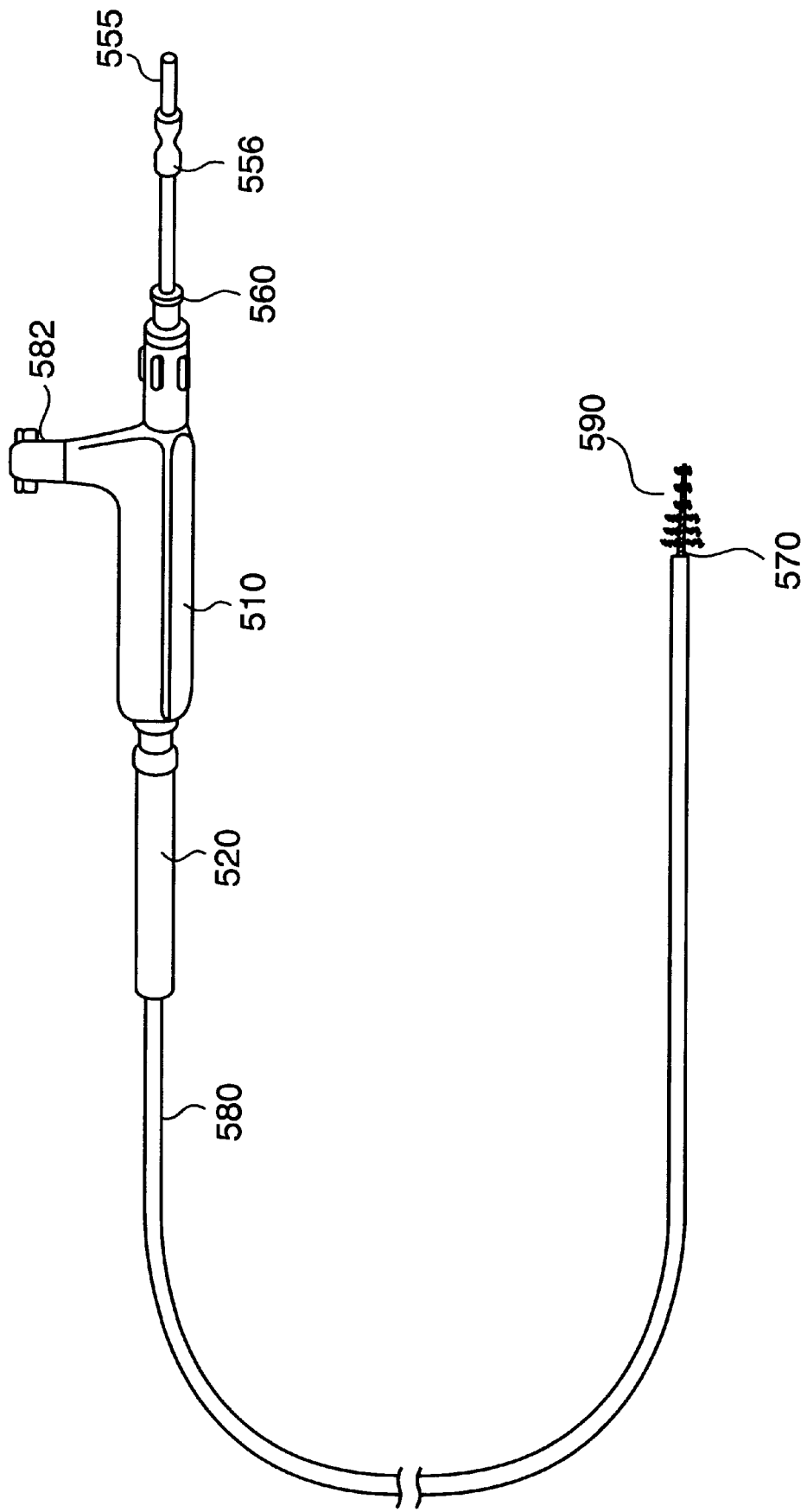
FIG. 5 depicts exemplary components of the system of FIG. 1.

An exemplary assembly will now be described with reference to FIG. 5. Referring to FIG. 5, the exemplary assembly includes a flexible drive shaft 570 having a brush head assembly 590 attached at its distal end and a power take off coupling 556 at its proximal end 555. Naturally, alternative means of connecting the flexible drive shaft 570 to the power take off 150 or 250, such as a chuck, a tightening screw, etc. may be employed. The flexible drive shaft 570 may be a small diameter flexible drive shaft sold by S. S. White Inc. of Piscataway, N.J. The brush head assembly 590 may include nylon fibers held in threaded metal wires. A dynamic seal 560 is provided around the flexible shaft 570 at a casing 510. The casing includes a fluid inlet port 582. The fluid inlet port 582 may be a known "luer lock" connector to which the tubing 320 of FIG. 3 may be coupled. A sheath 580 is provided through which the flexible shaft 570 extends. The sheath 580 may be a Teflon tube. A strain relief boot 520 may be provided over the proximal end of the sheath 580 to prevent crimping or breakage of the sheath 580 at its connection to the casing 510. The casing 510, luer lock 582, seal 560, boot 520, and Teflon sheath 580 may correspond to those components used on known endotherapy devices, such as Product Number KD-10Q-1 sold by Olympus Optical Co. Ltd. of Tokyo Japan.

Figure 6A:
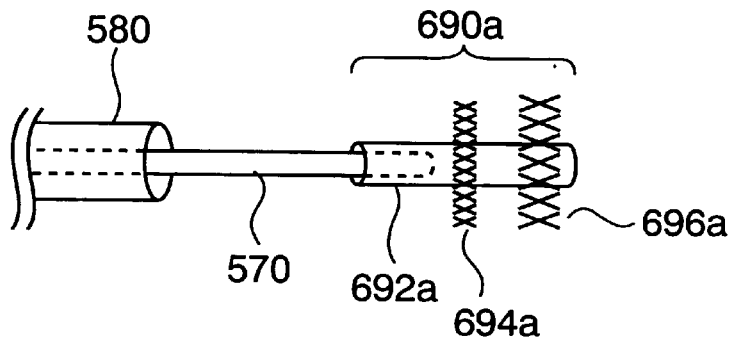
FIGS. 6a and 6b are side views of exemplary brush cleaning head assemblies which may be used in the system of FIG. 1.
Figure 6B:
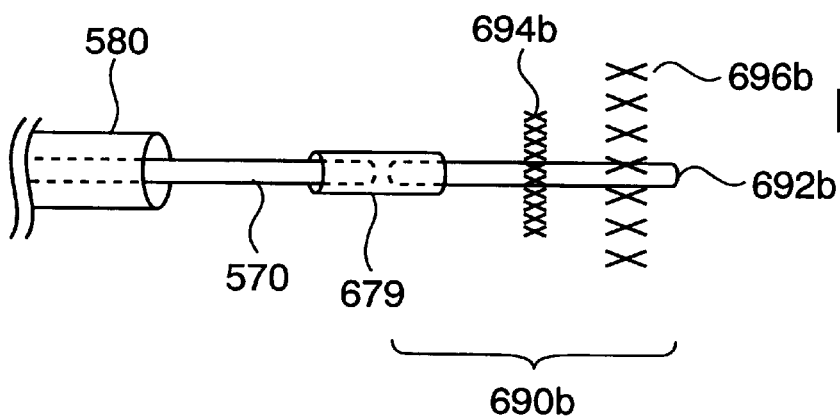
Figure 7A:
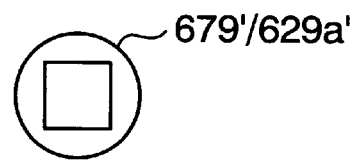
FIGS. 7a through 7c are cross-sectional views of exemplary flexible drive shaft-brush head assembly couplings which may be used in the system of FIG. 1.
Figure 7B:
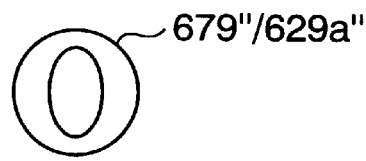
Figure 7C:
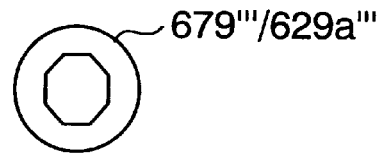
Figure 9A:
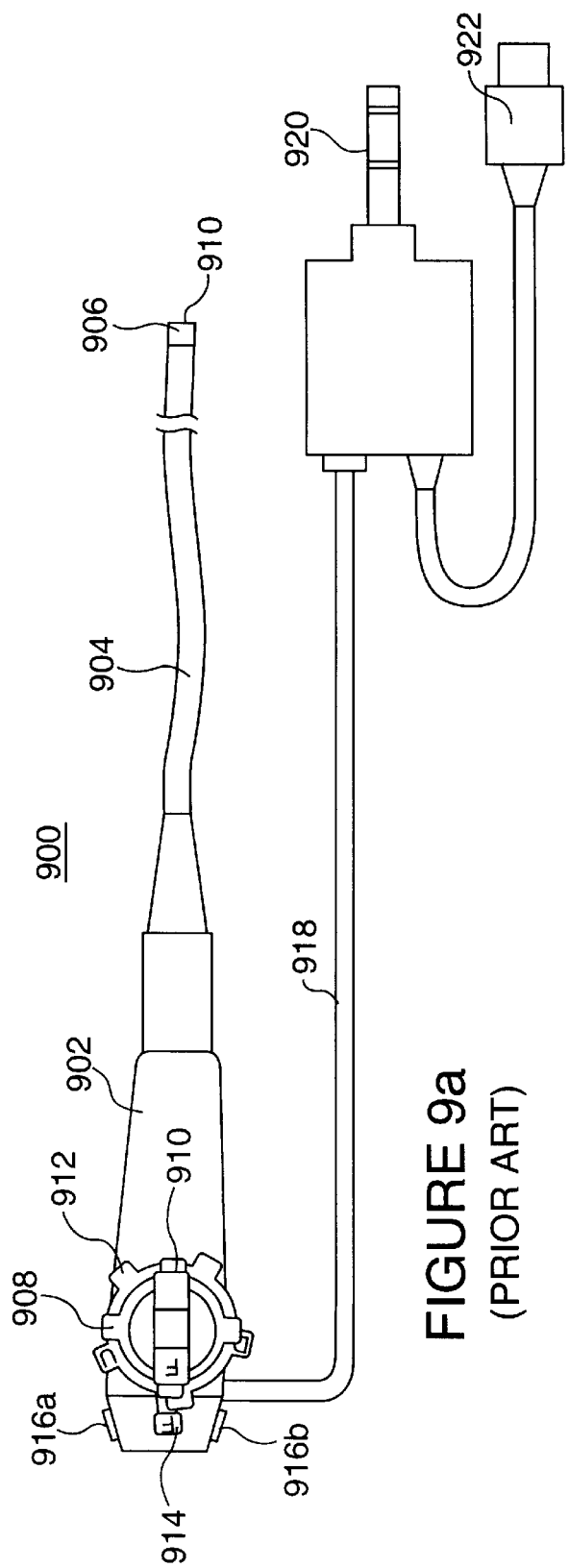
FIG. 9a depicts a conventional flexible video scope with which the present invention may be used.
Figure 9B:
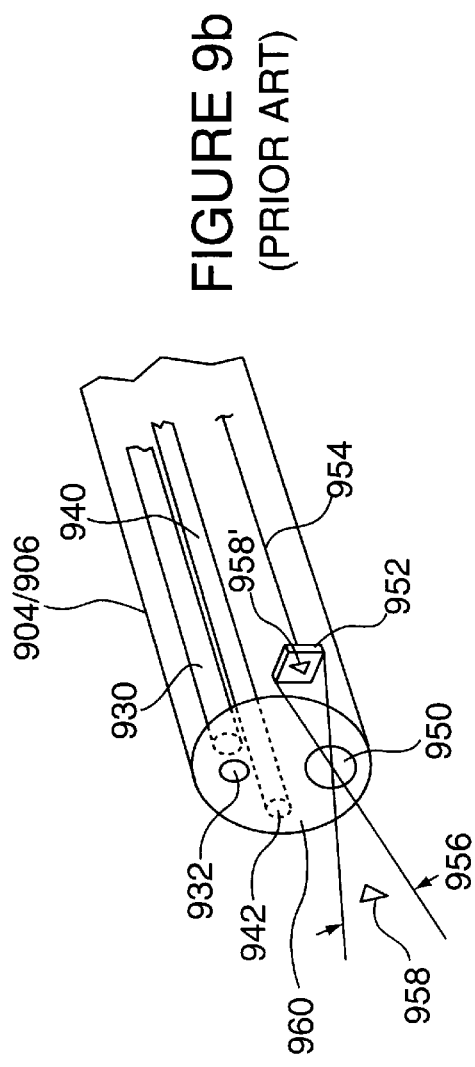

Different types of endoscopes often have different types of working channels, the diameter of which depends on the type of medical procedure for which the endoscope is used. Properties of the brush head 190, such as bristle configuration (e.g., stiffness, density, diameter, etc.), will be tailored to each type of working channel. Thus, referring to FIG. 5 for example, the brush 590 is preferably removably attached to the flexible shaft 570. Referring to FIG. 6a, a brush head assembly 690a may be provided with a void for accepting the distal end of the flexible shaft 570. The flexible drive shaft 570 may be connected to the brush head assembly by means of a friction fit, a crimping tool, or mated threads. Alternatively, as shown in FIG. 6b, a double female connector 679 may be used to accept the distal end of the flexible drive shaft 570 at one side, and the brush assembly 690 at the other side. Again, the connections between the connector 679 and the flexible drive shaft 570 and between the connector 679 and the brush head assembly 690b may be made by means of a friction fit, a crimping tool, or mated threads. If, in each of the embodiments shown in FIGS. 6a and 6b, a threaded connection is used, such a threaded connection may be oriented (e.g., right-handed threads) such that it is tightened, rather than loosened, by the rotation (e.g., right-handed) of the flexible drive shaft 570. If, on the other hand, in each of the embodiment shown in FIGS. 6a and 6b, a friction fit is used, the cross-sections of the flexible drive shaft 570 and brush head assembly 692a, or both the flexible drive shaft 570 and brush head assembly 690b, and the connector 679, should be shaped such that their resulting mating resists rotational slipping such as could occur if the mated elements had circular cross-sections. Examples of such mating shapes which resist rotational slipping may include a square 679'/692a' as shown in FIG. 7a, an ellipse 679"/692a" as shown in FIG. 7b, and an octagon 679'''/692a''' as shown in FIG. 7c.

Referring back to FIGS. 6a and 6b, the brush head assembly 690a/690b may include a first coarser and/or stiffer brush 696a/696b at its distal end and a second finer and/or softer diameter brush 694a/694b at a more proximal location. In this way, progressively finer cleaning is provided as the brush is passed through a working channel.

Figure 11:
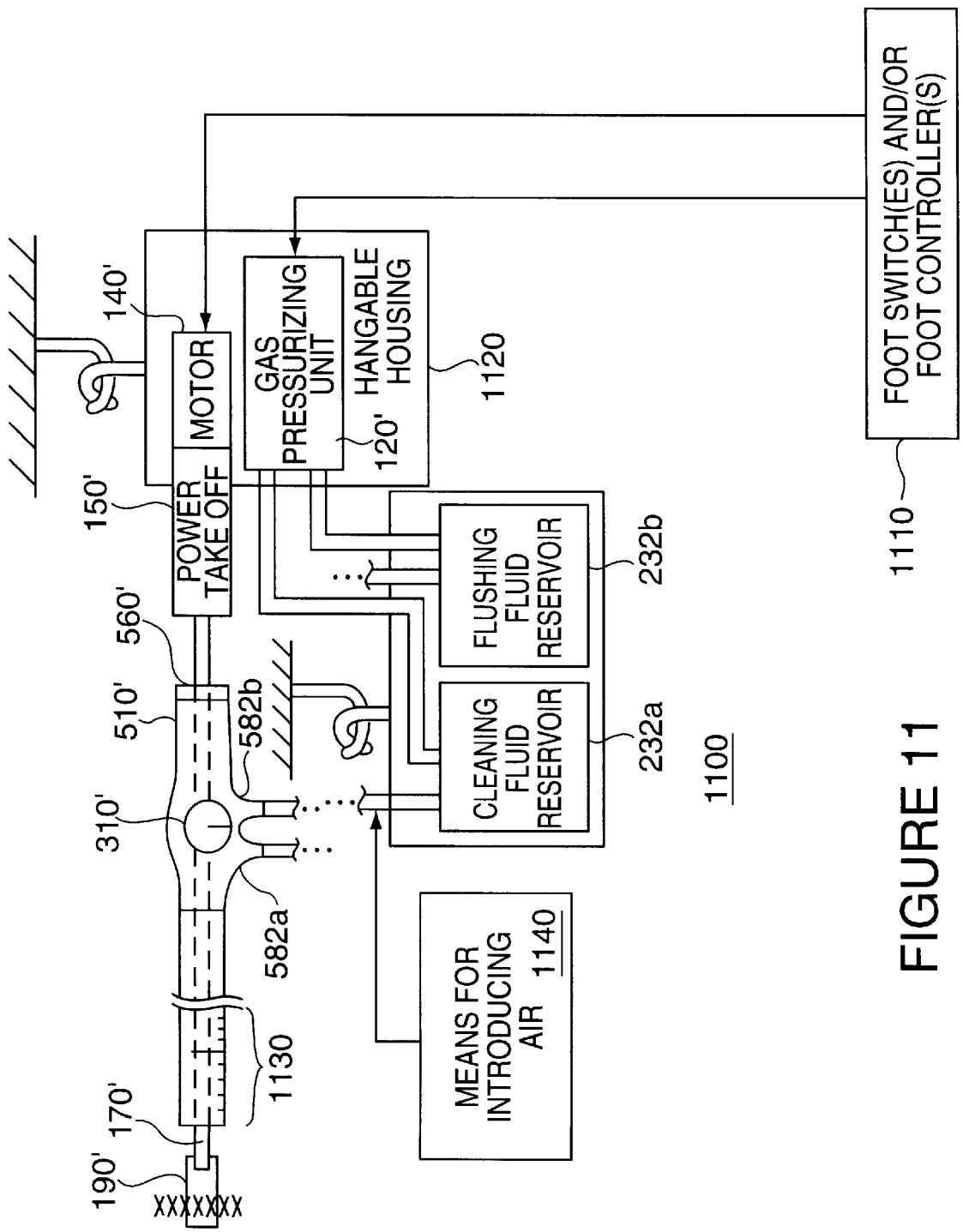
FIG. 11 depicts alternative features and components which may be used in an embodiment of the present invention.

FIG. 11 depicts alternative features and components, some or all of which may be used in an embodiment of the present invention. In a first alternative feature, the user input of the user input/output interface may include one or more switches or foot controllers 1110 for controlling (i) the ON-OFF state of the motor 140', (ii) the speed of the motor 140', and/or (iii) the ON-OFF state of the gas pressurizing unit 120'. In a second alternative feature, the housing 1120 accommodating the motor 140' the gas pressuring unit 120' and/or the fluid reservoir(s) 232a/232b may be provided as a hangable unit. In a third alternative feature, the source selection means 310' may be provided on a case 510' having two (2) luer locks 582a/582b. In a fourth alternative feature, the sheath is provided with insertion depth indication markings 1130. In a fifth alternative feature, means for introducing (e.g., mixing or injecting) air 1140 into cleaning fluid delivered from the reservoir may be provided to enhance cleaning action through alternating pulses of detergent and air.

OPERATION OF THE INVENTION

Having described both the functions of the present invention, and an exemplary structure embodying the present invention, an operation of the exemplary embodiment of the present invention is described in the context of cleaning a working channel of an endoscope.

After an endoscope has been used in a medical procedure, its working channel(s) may have become contaminated during a biopsy, a cauterizing procedure, an irrigation, an insufflation, or a suction. First, an appropriate brush head assembly 190 is coupled with the distal end of the flexible drive shaft 170. (Recall, e.g., FIGS. 6a through 7c.) Referring first to the generic system of FIG. 1, the flexible drive shaft 170 (See, e.g., element 570 of FIG. 5.) is coupled with the power take off 150 of the motor 140 by means of power take off coupling 156 (See, e.g., element 556 of FIG. 5.). In addition, the outlet tube of the cleaning fluid reservoir 130 (See, e.g., tube 320 of FIG. 3.) is coupled with the fluid inlet port 182 (See e.g., luer lock 582 of FIG. 5.) of the sheath 180. The motor 140 is started and its rotation may be set via the user input/output interface 116. (See, e.g., power switch 216a and rotary knob 216b of FIG. 2.) As the brush head is inserted into an end (distal or proximal) of the working channel, the gas pressuring unit 120 may be activated via the user input/output interface 116 such that cleaning fluid from the reservoir 130 is passed to the brush 190 via the fluid inlet port 182 and the sheath 180. Referring to FIG. 3, flushing fluid and/or cleaning fluid may be separately provided or provided in combination. The brush head assembly 190, the flexible shaft 170 and the sheath 180 are then passed (i.e., pushed) through the working channel. In addition, air may be injected into the detergent to enhance cleaning. (Recall, e.g., element 1140 of FIG. 11.) Finally, the motor 140 can be shut-off via user input/output interface 116 (or left on) and solely flushing fluid (e.g., water) can be directed (Recall selection means 310 of FIG. 3.) to rinse out the dislodged debris from the working channel as the brush head assembly 190, the flexible drive shaft 170 and the sheath 180 are pulled back out from the working channel. The movement of the brush head through the working channel may be controlled by a device such as the one disclosed in the Oaki patents discussed above.

Figure 10:
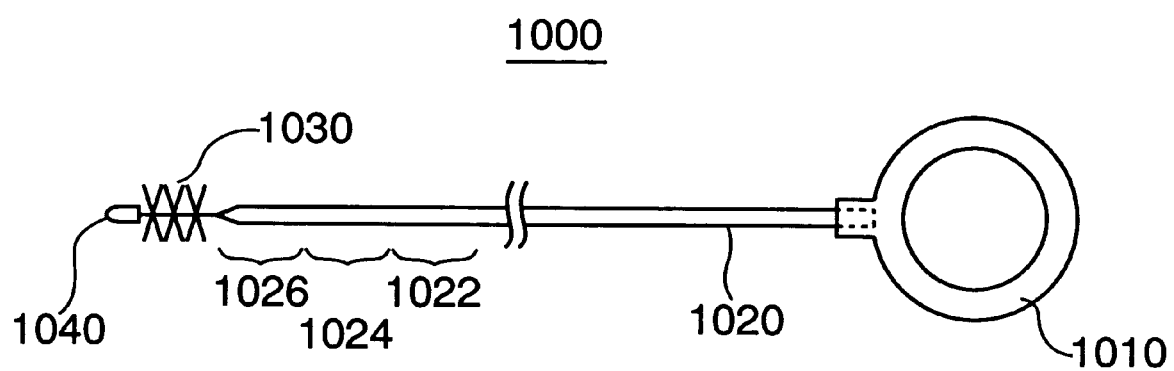
FIG. 10 is a side view depicting a conventional brush for manually cleaning working channels of endoscopes.

It is believed that a single pass through the working channel with a device embodying the present invention will provide better cleaning of the working channel than multiple passes with the known brush shown discussed above with reference to FIG. 10.

What is claimed is:

1. A device for cleaning a channel, the device comprising:
   a) a motor having a power take off;
   b) a gas pressurizing unit;
   c) a fluid reservoir having an inlet fluidly coupled with the gas pressurizing unit and an outlet;
   d) a flexible drive shaft having a first end connected with the power take off of the motor and a second end;
   e) a brush head assembly coupled with the second end of the flexible drive shaft;
   f) a flexible sheath through which the flexible drive shaft extends, having a fluid inlet port fluidly coupled with the outlet of the fluid reservoir; and
   g) a dynamic seal through which the flexible drive shaft extends, for sealing an end of the flexible tubular sheath.

2. The device of claim 1 further comprising means for controlling the motor.

3. The device of claim 1 further comprising means for controlling the gas pressurizing unit.

4. The device of claim 1 further comprising:
   h) means for controlling the motor; and
   i) means for controlling the gas pressurizing unit.

5. The device of claim 1 wherein the first end of the flexible drive shaft is connected with the power take off of the motor by means of a chuck.

6. The device of claim 1 wherein the flexible sheath is a Teflon tube.

7. The device of claim 1 wherein the fluid reservoir includes
   i) a first fluid reservoir for containing flushing fluid; and
   ii) a second fluid reservoir for containing cleaning fluid.

8. The device of claim 7 further comprising means for selecting a fluid source including
   i) a first inlet fluidly coupled with an outlet of the first fluid reservoir,
   ii) a second inlet fluidly coupled with an outlet of the second fluid reservoir,
   iii) an outlet fluidly coupled with the fluid inlet port of the flexible sheath, and
   iv) a selector for fluidly coupling one of (a) the first fluid inlet of the means for selecting, (b) the second fluid inlet of the means for selecting, (c) both the first and second fluid inlets of the means for selecting, and (d) neither of the first and second fluid inlets of the means for selecting, to the outlet of the means for selecting.

9. The device of claim 1 wherein the fluid inlet port of the flexible sheath is a luer lock connector.

10. The device of claim 1 wherein the brush head assembly includes
    i) a proximal end connected with the second end of the flexible drive shaft,
    ii) a distal end,
    iii) a first brush of coarse, stiff, bristles, and
    iv) a second brush of fine, soft, bristles, wherein the first brush is arranged on the brush head assembly between the distal end and the second brush.

11. The device of claim 1 wherein the brush head assembly is connected with the second end of the flexible drive shaft by means of a friction fit.

12. The device of claim 11 wherein the brush head assembly and the second end of the flexible drive shaft have mating cross sectional shapes such that rotational slip between the flexible drive shaft and the brush head assembly is prevented.

13. The device of claim 1 wherein the brush head assembly is connected with the second end of the flexible drive shaft by means of a threaded connection.

14. The device of claim 1 wherein the brush head assembly is connected with the second end of the flexible drive shaft by means of a crimped connection.

15. The device of claim 1 further comprising:
    h) a foot actuated controller for controlling at least one of the motor and the gas pressurizing unit.

16. The device of claim 1 wherein the flexible sheath includes markings for indicating an insertion depth.

17. A device for use with a system for cleaning a channel, the device comprising:
    a) a flexible drive shaft having a first end and a second end;
    b) a flexible sheath through which the flexible drive shaft extends, having
       i) a first end through which the first end of the flexible drive shaft extends, ii) a second end through which the second end of the flexible drive shaft extends, and iii) a fluid inlet port arranged between the first and second ends of the flexible sheath, closer to the first end of the flexible sheath than the second end of the flexible sheath; and c) a dynamic seal, provided on the first end of the flexible sheath, through which the first end of the flexible shaft extends.

18. The device of claim 17 wherein the flexible sheath is a Teflon tube.

19. The device of claim 17 wherein the fluid inlet port is a luer lock connector.

20. The device of claim 17 further comprising:

d) a brush head assembly removeably coupled with the second end of the flexible drive shaft.

21. A device for use with a system for cleaning a channel, the device comprising:

a) a flexible drive shaft having a first end and a second end;

b) a flexible sheath through which the flexible drive shaft extends, having a first end through which the first end of the flexible drive shaft extends, and a second end through which the second end of the flexible drive shaft extends;

c) a casing, having a first end and a second end, the first end of the casing being coupled with the first end of the flexible sheath, the casing including a fluid inlet port; and d) a dynamic seal, provided on the second end of the casing, through which the first end of the flexible shaft extends, wherein the second end of the flexible drive shaft is adapted to receive a cleaning brush.

22. The device of claim 21 further comprising:

e) a cleaning brush coupled with the second end of the flexible drive shaft.

* * * * *